United States Patent [19]

Sadun

[11] Patent Number: 4,826,308
[45] Date of Patent: May 2, 1989

[54] METHOD AND SYSTEM FOR DETECTING, CHARACTERIZING AND MONITORING OPTIC NERVE DISEASES

[75] Inventor: Alfredo A. Sadun, San Marino, Calif.
[73] Assignee: University of Southern California, Los Angeles, Calif.
[21] Appl. No.: 815,216
[22] Filed: Dec. 31, 1985
[51] Int. Cl.$^4$ .................. A61B 3/02; G02C 7/12
[52] U.S. Cl. ...................... 351/49; 351/232
[58] Field of Search .............. 351/49, 215, 232, 234, 351/235; 350/407

[56] References Cited

U.S. PATENT DOCUMENTS

| | | | |
|---|---|---|---|
| 3,074,397 | 1/1963 | Gernet | 351/49 |
| 3,944,346 | 3/1976 | Shindler | 351/49 |
| 4,145,123 | 3/1979 | Krahn et al. | 351/24 |
| 4,188,097 | 2/1980 | Holladay | 351/232 |
| 4,264,154 | 4/1981 | Petersen | 351/49 |

FOREIGN PATENT DOCUMENTS 706306  3/1954  United Kingdom .

OTHER PUBLICATIONS

"Amsler Charts", The Optician, vol. CXXII, pages XVII and 384, Nov. 2, 1951.
Article by Alfredo A. Sadun & Michael Wall entitled "Threshold Amsler Grid Testing: Cross Polarizing Lenses Further Enhance Yield" published in Archieves of Ophthalmology, vol. 104, pp. 520-523 (1986).
Article by Mainster & Dieckert entitled "A simple Haploscopic Method for Quantitating Color Brightness Comparison" published in American Journal of Ophthalmology, vol. 89, No. 1, pp. 58-61 (1980);
Article entitled "Brightness-Sense and Optic Nerve Disease" published in Archives of Ophthalmology, vol. 103, pp. 39-43 (Jan., 1985).

Primary Examiner—Deborah L. Kyle
Assistant Examiner—Michael J. Carone
Attorney, Agent, or Firm—Pretty, Schroeder, Brueggemann & Clark

[57] ABSTRACT

A method and system are provided for detecting, characterizing and monitoring eye diseases and, particularly, optic nerve diseases, by determining the difference in relative brightness sensed by the two eyes. The method utilizes eyeglasses having a pair of cross-polarizing lenses selectively adjustable for blocking or admitting light into each eye. The patient observes an illuminated test object while looking through the eyeglasses at maximum luminance. By adjusting the relative polarization of the lenses for the eye in which the test object appears the brightest, while occluding the other eye, the amount of brightness sensed by that eye can be compared to the other eye. If there is a disparity in brightness-sense between the eyes within certain pre-established ranges, the nature of the eye disease can be detected and specifically characterized, and its progression or resolution can be monitored.

9 Claims, 1 Drawing Sheet

U.S. Patent
May 2, 1989
4,826,308
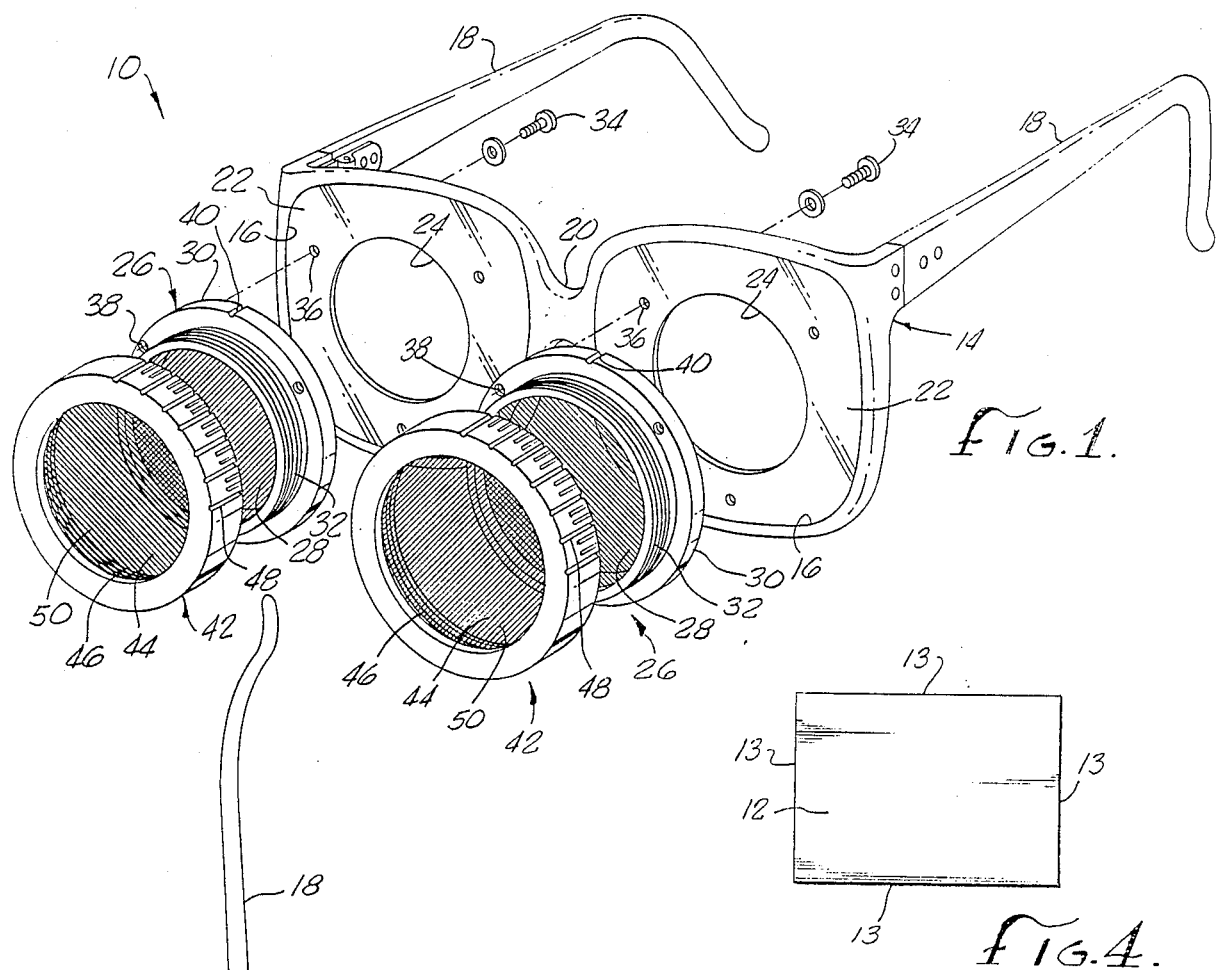
fig.1.
fig.4.
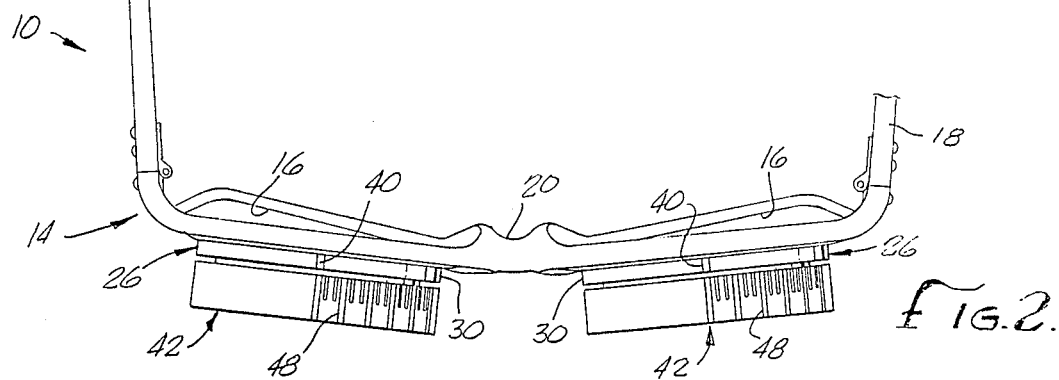
fig.2.
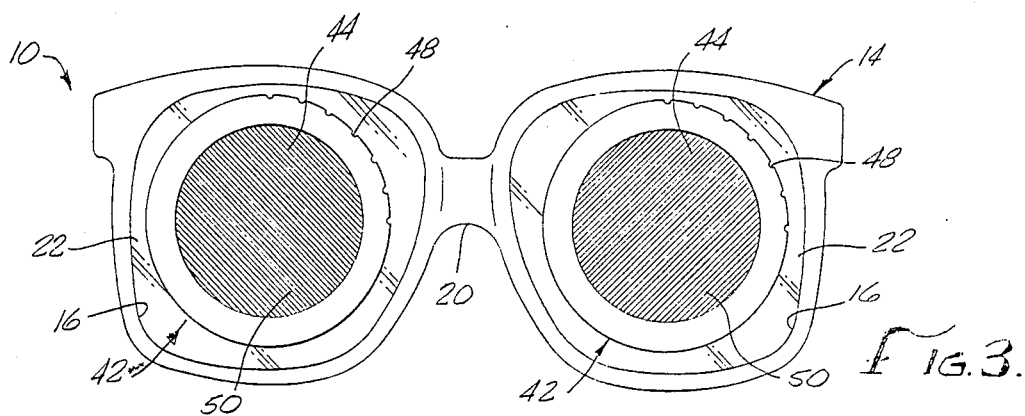
fig.3.

METHOD AND SYSTEM FOR DETECTING, CHARACTERIZING AND MONITORING OPTIC NERVE DISEASES

BACKGROUND OF THE INVENTION

This invention relates to a method and system for detecting, characterizing and monitoring eye diseases and, particularly, optic nerve diseases, by determining the relative difference in brightness sensed by the two eyes.

Patients who have developed some sort of eye disease typically suffer a loss of visual acuity, an impairment of their visual field, a disparity in color vision, irregular pupillary responses to light, or a combination of two or more of these symptoms. Traditional methods of detecting eye diseases, therefore, have been concerned with measuring the person's visual acuity, visual field, color vision and pupillary responses to light. Additionally, recording of visual evoked responses and measurement of contrast sensitivity have been used to evaluate eye functions and to detect the presence of disease. Of all the above methods, measurement of visual acuity generally has been the most widespread method adopted and used in the neuro-ophthalmic evaluation of eye diseases.

Experience has shown in many instances, however, that measurement of visual acuity is insufficient to detect optic nerve disease. For example, post mortem studies have shown extensive dropout of optic nerve axons in some patients whose visual acuity and general eye examinations have been entirely normal. In one post mortem study of a patient reportedly having no clinical evidence of impaired eye functions, it was estimated that one half of the patient's optic nerve axons had been lost from glaucoma. Additionally, patients who have been diagnosed as having optic neuritis, a form of optic nerve disease, may recover their normal vision, yet still exhibit dysfunction as detected by further clinicial and laboratory tests. Thus, it is apparent that the most widespread method of detecting eye disease is imperfect and inadequate to determine the existence of optic nerve disease.

Measurement of visual acuity also may fail to distinguish among several possible ophthalmological diseases. For example, a patient may have a cataract causing poor vision. If the patient also has optic nerve disease, an operation to remove the cataract would be a useless procedure and pose an unnecessary risk. Unfortunately, the cataract which is causing the poor vision also prevents the ophthalmologist from examining the back of the eyes to attempt to detect the existence of optic nerve disease. Another type of problem may involve a patient with inflamation at the back of the eye, which could be caused by a disease of the retina or of the optic nerve. Even if the ophthalmologist is able to determine that optic nerve disease is present, there are several types of optic nerve disease. Visual acuity tests thus far have been inadequate in distinguishing between the types of optic nerve disease and, further, in monitoring the progression or resolution of the disease once it has been identified.

In 1980, Manister and Dieckert disclosed that color brightness comparison of the eyes may be a useful technique for detecting monocular or asymmetric deficits in optic nerve or macular function. Their method involved presenting a brightly colored test objects to a patient's two eyes and determining whether the eyes perceived the object to be of equal brightness, as described in their article in *American Journal of Ophthalmology*, Vol. 89, No., 1, pages 58-61 (1980). To determine color brightness differences, they used two polarized trial lenses in a standard trial frame positioned in front of the patient's eyes. The Mainster and Dieckert method, however, focuses on color brightness differences involving red, blue and yellow targets illuminated in a stereoscopic viewer, where an inter-eye disparity in hue perception admittedly renders the method of limited value. Moreover, even if an optic nerve disorder is indicated by a color brightness disparity between the two eyes through their method, there is no disclosure in their article as to how to relate these findings to the nature or extent of the disease. They did not run a clinical study which could suggest how their test results could help in distinguishing among the several types of optic nerve disorders. The device used by Mainster and Dieckert also allows extraneous light to enter laterally between the trial lenses, which obfuscates accurate readings and detracts from the ability to regulate luminance to each eye. In addition, their trial frame system is clumsy and requires frequent recalibration.

Accordingly, there has existed a definite need for a further method of detecting, characterizing and monitoring optic nerve diseases which is not dependent upon the traditional symptoms manifested by a person suffering from eye disease, such as loss of visual acuity, reduction of visual field, disparity in color vision and irregularity of pupillary responses to light. The present invention satisfies this need and provides further related advantages.

SUMMARY OF THE INVENTION

The present invention provides a method and system for detecting, characterizing and monitoring eye diseases and, particularly optic nerve diseases, by determining the difference in brightness sensed by the two eyes. The method utilizes eyeglasses having a pair of cross-polarizing lenses selectively adjustable for blocking or admitting light into each eye. By adjusting the relative polarization of the lenses, it can be determined whether the brightness sensed by each eye is the same or different. If there is a disparity between the two eyes in brightness-sense within certain pre-established ranges, it can provide an indication that optic nerve disease is or is not present. The method of this invention furthermore is intended to be simple and inexpensive to implement, and relatively reliable in result.

The eyeglasses used in practicing the method of this invention comprise a frame having two oculars in visual alignment with a patient's eyes. A pair of supports, extending from the oculars, wrap around the patient's ears and position the eyeglasses securely in front of the patient's eyes. A substantially transparent, polarized inner lens fixed against rotation is mounted in each ocular. Another substantially transparent, polarized outer lens is rotatably mounted in front of each fixed inner lens. Rotation of the outer lenses with respect to the fixed inner lenses over a ninety degree angle of rotation controls the amount of light permitted to collectively pass through the lenses into each eye.

The method of the present invention utilizes the eyeglasses described above and comprises the steps of setting the outer lenses at zero degrees rotation with respect to the inner lenses to permit maximum light transmission to the eyes, and then positioning the eyeglasses on the patient. The patient is requested to observe an illuminated test object, such as a plain sheet of white paper, while an ophthalmologist alternately occludes the patient's eyes to determine in which eye the illuminated object appears the brightest. The ophthalmologist then rotates the adjacent outer lens for the eye in which the illuminated object appeared the brightest away from zero degrees rotation with respect to the inner lens to decrease luminance until the illuminated object is sensed substantially equally bright in the two eyes. The amount of rotation of the adjacent outer lens with respect to the inner lens may then be quantified to determine the relative sense of brightness of the two eyes. The relation of $COS^2\theta$ describes the extent of light transmission as a function of the angle between the polarized lenses. If the object appeared brighter in one eye than in the other, then the eye in which the object appeared less bright is a target for consideration as one in which optic nerve disease may be present. The reduction of brightness-sense in the eye less perceptive of brightness is quantified in terms of its percent brightness of the other eye. This percentage figure indicating the relative brightness-sense of the two eyes is correlated with a particular category of eye disease in which the inventor has empirically established that such disease is commonly present when the percentage of relative brightness sense of the two eyes is within the particular range for that disease. One may then determine whether or not optic nerve disease is present. If it is present, the ophthalmologist then examines other eye functions and/or further monitors the disease by periodically determining brightness-sense to characterize the type of optic nerve disease. Once the disease is identified its progression or resolution may be monitored by periodically repeating the above procedures in the doctor's office.

Another aspect of the present invention includes a system for detecting, characterizing and monitoring optic nerve disease by determining the relative sense of brightness of the left and right eyes. The system comprises an illuminated object for viewing by the patient, and a pair of eyeglasses like those described above. The system further comprises means for quanitifying the amount of relative brightness sensed by each eye, and means for correlating the relative sense of brightness of the two eyes with a particular category of optic nerve disease.

Other features and advantages of the present invention will become apparent from the following detailed description, taken in conjunction with the accompanying drawings, which illustrate, by way of example, the principles of the invention.

BRIEF DESCRIPTION OF THE DRAWINGS

The accompanying drawings illustrate the eyeglasses used in the method of the invention. In such drawings:

FIG. 1 is an exploded view of the eyeglasses having cross-polarizing lenses used in the method of the present invention;

FIG. 2 is a plan view of the eyeglasses of FIG. 1;

FIG. 3 is a front elevational view of the eyeglasses; and

FIG. 4 is a front view of a sheet of white paper for observation through the eyeglasses by a patient.

DETAILED DESCRIPTION OF THE PREFERRED EMBODIMENT

The present invention is embodied in a method of detecting, characterizing and monotoring eye diseases and, particularly, diseases of the optic nerve. The method utilizes a pair of eyeglasses, generally referred to by the reference numeral 10, for use in measuring the relative sense of brightness of the two eyes. A reduction in a patient's brightness-sense in one eye as compared to the other has been found to be a symptom having a high degree of correlation with the presence of an ophthalmological disease. Depending upon the inter-eye disparity in brightness-sense, the type of disease can be characterized and thereafter monitored through its progression or resolution. The method of this invention furthermore can be quickly and inexpensively carried out, and it can detect, characterize and monitor certain eye diseases where other methods have failed.

The equipment used to practice the method of this invention includes the eyeglasses 10 and an illuminated test object 12 for viewing through the eyeglasses by a patient to be tested for eye disease. The object preferably comprises a plain sheet of white paper, as illustrated in FIG. 4, having side margins 13 and illuminated by normal room lighting. Other suitable light reflecting objects or the like may be used as desired.

The eyeglasses 10 comprise a frame 14 including a pair of oculars 16 with elongated supports 18 extending away from the oculars for resting on the patient's ears. A bridge 20 separates the oculars and rests on the patient's nose. The bridge and two supports function together to position and retain the eyeglasses on the patient, with the oculars arranged in visual alignment with the patient's eyes. Within each ocular is a mounting plate 22 having a substantially circular opening 24 in its center to permit unobstructed vision through the oculars. The mounting plate is substantially transparent and snap-fits within the oculars, as would a normal eyeglass lens.

An inner lens mount 26 carrying a substantially transparent polarized inner lens 28 is mounted to the anterior or front surface of each of the plates 22. The inner lens mount is substantially cylindrical and has a radially outwardly extending flange 30 at the rear part of the mount, and an externally threaded outer surface 32 at the front part of the mount. The inner lens mount is secured to the plate by screws 34 extending through holes 36 and 38 in the plate and internally threaded holes in the flange, respectively, to thereby prevent rotation of the inner lens mount with respect to the plate and eyeglasses 10. A reference notch 40 also is provided in the outer surface of the flange, the function of which will be explained below. While separate polarized inner lenses are provided for each eye in the preferred embodiment, a single sheet of polarized lens material can be provided, if desired, in front of both eyes instead. With this construction, the single polarized lens is mounted within a single inner lens mount constructed and arranged for mounting to the frame to cover both eyes.

An outer lens mount 42 carrying a substantially transparent polarized outer lens 44 is rotatably mounted to each of the inner lens mounts 26. The outer lens mount is substantially cylindrical and has an internally threaded surface 46 at the rear part of the mount, with the polarized outer lens secure within the front part of the mount. The internal threads of the outer lens mount are adapted to mate with the external threads 32 of the inner lens mount so that the inner and outer lens mounts are threadedly attached to each other. To install the mounts, the outer lens mount preferably is threaded onto the inner lens mount until the threads bottom out, and then the outer lens mount is backed off about a quarter to three quarters of a turn. This permits the outer lens 44 to rotate with respect to the inner lens 28 a sufficient rotational amount for enabling practice of the present invention as described below. The external surface of the outer lens mount contains a plurality of measuring notches 48 which, in the preferred embodiment, are spaced apart every fifteen degrees over a ninety degree segment of the external surface of the outer lens mount. That is, there are seven measuring notches corresponding to locations on the outer lens mount of 0, 15, 30, 45, 60, 75 and 90 degrees rotation. In the preferred embodiment each space between two notches is further divided with two markings so that each incremental measure is 5 degrees. The reference notch 40 preferably is positioned at the twelve o'clock position on the inner lens mount, as best shown in FIG. 1, to permit easy viewing with respect to the measuring notches 48.

The polarized inner and outer lenses 28 and 44 each have polarizing gratings, as illustrated by the parallel lines 50, which cooperate to selectively control the amount of light permitted to collecting pass through the inner and outer lenses. Thus, when the polarizing gratings of the inner and outer lenses are parallel to each other, the maximum amount of light is permitted to collectively pass through the lenses. When the polarizing gratings are orthogonal, however, the minimum amount of light is permitted to collectively pass through. To determine the relative position of the polarizing gratings of the outer lens with those of the inner lens, the reference notch 40 on the inner lens mount 26 and the measuring notches 48 on the outer lens mount 42 can be positioned accordingly. It is arranged that when the first measuring notch representing zero degrees rotation aligns with the reference notch, the polarizing gratings are in parallel to permit maximum light transmission. Similarily, when the seventh measuring notch representing ninety degrees rotation aligns with the reference notch, the polarizing gratings are orthogonal for minimum light transmission. For purposes of illustration, FIG. 1 shows the polarizing gratings in an orthogonal relationship, with the seventh measuring notch aligned with the reference notch.

The eyeglasses 10 described above, including the frame 14, inner lens mounts 26 and outer lens mounts 42, can be constructed from rigid plastic or other suitable lightweight materials. The inner and outer lenses 28 and 44 are constructed from a substantially transparent polarized material. If desired, the measuring notches 48 can be increased in number to provide a more refined measurement of relative rotation between the outer and inner lens mounts. In practicing the method of this invention, it has been found that measuring notches spaced apart about every five degrees is satisfactory and provides a sufficient degree of accuracy. The eyeglasses are intended to be inexpensive to manufacture and capable of use at home by a patient, as directed by the patient's ophthalmologist, to monitor the progression or resolution of an optic nerve disease once it has been identified.

The construction of the eyeglasses 10 substantially prevents extraneous light from entering between the frame 14 and the inner and the outer lenses 28 and 44. Unlike open trial frames and lenses, in which significant amounts of light may reach the patient's eyes without passing through the polarized lenses, the eyeglasses of this invention are designed to minimize spaces between the lenses and the frame. This results in an improved ability of the eyeglasses to regulate luminance to each eye. The eyeglasses also utilize relatively large polarizing lenses and a vertex distance of less than 10 millimeters, to increase the size of the visual field for improved accuracy and reliability. Since the inner lens is fixed in reference to the frame, repeated calibrations are not necessary.

The method of detecting, characterizing and monitoring optic nerve disorders by determining the relative amount of brightness sensed by the patient's eyes is as follows. The eyeglasses 10 are positioned in front of the patient's eyes, with the outer lens mounts 42 positioned at zero degrees rotation with respect to the inner lens mounts 26 to permit maximum light transmission through the inner and outer lenses 28 and 44. As the patient observes the illuminated test object 12 through the eyeglasses, such as a plain sheet of white paper under normal room lighting conditions, the ophthalmologist alternately occludes each eye and asks the patient to identify the eye in which the test object appears the brightest. If no such identification is made by the patient, for example, because the test object is sensed as equally bright by both eyes, then it can be determined that no optic nerve disorders are present, or that an optic nerve disorder has affected both eyes equally. If the patient identifies one eye in which the test object appears the brightest, then this is a sign that something may be wrong in the other eye in which the test object appeared dimmer or less bright.

To determine the amount of reduced brightness-sense in the affected eye, the ophthalmologist rotates the outer lens mount 42 in which the test object 12 appeared the brightest, i.e. the unaffected eye, away from zero degrees rotation to decrease luminance in that eye and match it with the affected eye. After decreasing luminance in that eye, the eyes are again alternately occluded while the patient identifies the eye in which the test object appears the brightest. If the patient still identifies the unaffected eye, the luminance in that eye is decreased further. However, if the patient now identifies the affected eye, then the luminance in the unaffected eye is increased slightly by rotating the outer lens mount back a little toward zero degrees rotation. The above procedure is continued until the patient indicates that the test object is sensed substantially equally bright in both eyes. Throughout this procedure, the outer lens mount of the affected eye remains untouched and at zero degrees rotation with respect to its adjacent inner lens mount to permit maximum luminance through the lenses 28 and 44 into that eye. The entire procedure described above may be repeated to establish patient reliability.

After the above procedure has been completed, the ophthalmologist determines the amount that the outer lens mount 42 of the unaffected eye has rotated with respect to the inner lens mount 26. By way of example, if the outer lens mount has rotated thirty degrees, i.e., to the third measuring notch 48, then the amount of light transmitted to that eye has been reduced by a factor of about twenty four percent (24%). In other words, the brightness-sense of the affected, diseased eye is approximately seventy six percent (76%) of the brightness-sense of the unaffected, normal eye. This conversion is calculated by the following equation:

$$I = \cos^2 \theta \times 100\%$$

where I equals brightness-sense of the affected eye and θ equals the number of degrees that the outer lens mount has rotated away from zero degrees rotation. Thus, when θ equals zero degrees, the polarizing gratings 50 are parallel and the brightness-sense should be one hundred percent (100%). If θ equals ninety degrees, then the polarizing gratings are orthogonal and the brightness-sense should be zero percent (0%).

The ophthalmologist can utilize the percent difference in brightness-sense between the two eyes as a test for the nature of the ophthalmological disorder from which the patient may be suffering. Empirical studies by the inventor reported in an article entitled "Brightness-Sense and Optic Nerve Disease" published in the *Archives of Ophthalmology*, Volume 103, pages 39–43, January, 1985, have shown that the degree of reduced brightness-sense of one eye as compared to the other is directly related to several specific ophthalmological disorders. The following table reflects the results of one such empirical study involving over 100 patients:

| Disease Category | Relative Mean Brightness-Sense Of Affected Eye (%) | Range (%) |
| --- | --- | --- |
| No disease | 99 | 80–100 |
| Optic neuritis (recent onset) | 25 | 2–40 |
| Optic neuritis (old/resolved) | 45 | 25–75 |
| Anterior ischemic optic neuropathy | 30 | 15–45 |
| Compressive optic neuropathy (tumors, etc.) | 17 | 1–35 |
| Retinal diseases (non-macular) | 90 | 80–100 |
| Retinal diseases (macular) | 65 | 35–85 |
| Cataracts | 93 | 80–100 |

The figures set forth in the above table reflect the approximate ranges of brightness-sense of an eye suffering from the disease indicated for that range according to the inventor's previously identified research. For example, an affected eye having a brightness-sense that is between two and seventy-five percent (2–75%) of the unaffected eye would be interpreted by an ophthalmologist aware of the above table as an indication of optic nerve disease. It is noted from the table that the patient may have one of several optic nerve diseases, such as optic neuritis of recent onset, old or resolved optic neuritis, anterior ischemic optic neuropathy, or compressive optic neuropathy from, for example, a tumor. All of these diseases have a range of reduced brightness-sense scores that would indicate a disease of the optic nerve. In such instances, the ophthalmologist can determine generally that the patient has an optic nerve disorder, but must further monitor the disease to be able to pinpoint its precise nature.

For example, if optic neuritis of recent onset is present, the patient will have a very low brightness-sense score, usually about twenty-five percent (25%) of the other eye. After subsequent follow-up visits, the patient will show a steady increase in his brightness-sense score over a period of approximately four to eight months. If old or resolved optic neuritis is present, the patient will usually have substantially 20/20 vision and a higher brightness-sense score averaging about forty-five percent (45%). The patient otherwise will appear normal, and the brightness-sense score probably will not fluctuate over a period of time thereafter. If anterior ischemic optic neuropathy is present, the patient also probably will have an altitudinal visual field loss associated with his brightness-sense score of approximately 30. This can be detected by known methods. Finally, if compressive optic neuropathy (tumor) is present, the patient will have a progressively decreasing brightness-sense score over the following several months. A patient with compressive optic neuropathy normally has the lowest brightness-sense score, averaging about seventeen percent (17%).

It is important to note from the table that patients who are normal or who have cataracts do not show any significant impairment of brightness-sense. Additionally, patients who have retinal diseases and, in particular, macular degeneration, show only a slight impairment of brightness-sense. This information assists ophthalmologists in distinguishing between several possible ophthalmological diseases. One of the most common problems of distinguishing among diseases that confronts the ophthalmologist is the cataract patient who may also have optic nerve disease. Prior to extracting the cataract, which may be the explanation for the patient's poor vision, the ophthalmologist should rule out the possiblility of optic nerve disease which would make the operation fruitless and, therefore, expose the patient to an unnecessarily dangerous risk. Unfortunately, the cataract that precludes good vision for the patient also precludes an adequate examination of the back of the eye by the ophthalmologist. As noted from the table, however, the presence of a cataract does not produce a decrease in brightness-sense of that eye. Accordingly, the ophthalmologist may simply determine the patient's brightness-sense in the eye with the cataract, using the eyeglasses and method described above, to screen for the disease. An equal brightness sense in both eyes (high score) suggests the absence of optic nerve disease, while a low brightness-sense score in the cataract affected eye relative to the other eye would caution the ophthalmologist that the eye has developed an optic nerve disease as well as a cataract, and that surgical cataract extraction is probably not advisable.

A related problem exists in patients who have inflammation of the back of the eye which may be the result of either a retinal disease (such as central serous maculopathy) or an optic nerve disease. As can be seen from the table, however, retinal diseases generally produce only a minimal loss of brightness-sense, while optic nerve diseases tend to cause a rather severe loss of brightness-sense. Moreover, a retinal disease usually produces a great impairment of visual acuity, while optic nerve disease produces only a minimal loss, if any, of visual acuity. Thus, the method of the present invention provides a convenient and inexpensive method for detecting the presence of optic nerve disease generally, and then diagnosing the specific type of optic nerve disease upon monitoring the disease during follow-up visits by the patient. Additionally, the method of this invention assists the ophthalmologist in distinguishing among a variety of several ophthalmological diseases.

In addition to detecting the presence of optic nerve disease, the method of this invention also provides for monitoring diseases of the optic nerve. This is accomplished by repeatedly obtaining the patient's brightness-sense score over a period of time after initial diagnosis of a disease using the method described above. For example, patients with optic neuritis of recent onset will show steady improvement of their brightness sense in the affected eye on a weekly basis. On the other hand, patients with tumors on the optic nerve, i.e., compressive optic neuropathy, will show a steady decline of their brightness-sense score if the tumor is growing. In the latter instance, an ophthalmologist may choose to operate on an optic nerve tumor which is growing steadily and rapidly, and producing a steady decline of brightness-sense scores, while conservatively following a tumor that is not producing a steady decline, possibly treating it with non-surgical methods. The ophthalmologist also can evaluate the effect of surgical or non-surgical treatment of optic nerve disorders by periodically testing the brightness-sense of the affected eye by using the eyeglasses and method described above. Because the eyeglasses are intended to be relatively inexpensive and affordable, the procedure of monitoring the disease may be inexpensively carried out at home, under the direction of the ophthalmologist, to reduce the cost of follow-up visits.

Another aspect of the present invention includes a system for detecting, characterizing and monitoring optic nerve disease. The system comprises the illuminated test object 12 for viewing by the patient and the eyeglasses 10 like those described above. The eyeglasses include mean for quantifying the amount of relative brightness sensed by each eye which, in the preferred embodiment, are the plurality of measuring notches 48 on the outer lens mount 42 and the reference notch 40 on the inner lens mount 26. The system further includes means for correlating the relative sense of brightness of the two eyes with a particular category of optic nerve disease which, in the preferred embodiment, is the table identifying various optic nerve diseases that likely are present when the relative brightness sensed by the affected eye is within the range set forth in the table for that disease.

From the foregoing, it will be appreciated that the method of this invention can be quickly and inexpensively carried out to detect, characterize and monitor optic nerve diseases by determining the amount of relative brightness sensed by the two eyes. By adjusting the relative polarization of the inner and outer lenses 28 and 44, it can be quickly determined whether the brightness sensed by each eye is the same or different and, therefore, whether there is an indication for optic nerve disease. The invention further provides a system for detecting, characterizing and monitoring optic nerve disease in accordance with the method described.

While a particular form of the invention has been illustrated and described, it will be apparent that various modifications can be made without departing from the spirit and scope of the invention. Accordingly, it is not intended that the invention be limited, except as by the appended claims.

I claim:

1. A method of detecting eye disease in a patient by determining the difference in relative brightness sensed by the two eyes, using eyeglasses of the type having a polarized inner lens mounted against rotation in front of the oculars of the eyeglasses, and a pair of polarized outer lenses mounted for rotation with respect to and in visual alignment with the oculars, the inner lens and outer lenses having their polarizing gratings in parallel for maximum light transmission when the outer lenses are at zero degrees rotation with respect to the inner lens, and the polarizing gratings being orthogonal for minimum light transmission when the outer lenses are at ninety degrees rotation with respect to the inner lens, said method comprising the steps of:

(a) providing an illuminated object for viewing;
(b) setting the outer lenses at zero degrees rotation with respect to the inner lens to permit maximum light transmission to the eyes;
(c) positioning the eyeglasses in front of the patient's eyes;
(d) alternately occluding the eyes to identify the eye in which eye the illuminated object appears brighter, this eye being referred to as the unaffected eye and the other eye being referred to as the affected eye;
(e) rotating the adjacent outer lens for the unaffected eye away from zero degrees rotation with respect to the inner lens to decrease luminance until the illuminated object is sensed by the patient as being substantially equally bright in both eyes;
(f) quantifying the amount of rotation of the outer lens for the unaffected eye to thereby determine the amount of reduced brightness-sense of the affected eye as compared with the unaffected eye; and
(g) correlating the amount of reduced brightness-sense of the affected eye with one or more categories of eye disease in accordance with the following table as an indication of eye diseases afflicting the affected eye:

| TYPE OF EYE DISEASE | AMOUNT OF REDUCED BRIGHTNESS-SENSE OF AFFECTED EYE (%) | OTHER CONSIDERATIONS |
| --- | --- | --- |
| No disease | 80–100 | No significant inter-eye brightness-sense disparity |
| Optic neuritis (recent onset) | 2–40 | Brightness-sense increase over next 4–8 months |
| Optic neuritis (old/resolved) | 25–75 | 20/20 vision; no change in brightness-sense |
| Anterior ischemic optic neuropathy | 15–45 | Accompanied by altitudnal visual field loss |
| Compressive optic neuropathy | 1–35 | Brightness-sense reduction over next several months |
| Retinal diseases (non-macular) | 80–100 | Accompanied by poor visual acuity |
| Retinal diseases (macular) | 35–85 | Accompanied by poor visual acuity |
| Cataracts | 80–100 | No significant inter-eye brightness-sense disparity |

2. A method of detecting eye disease in a patient by determining the difference in relative brightness sensed by the two eyes, using eyeglasses of the type having a polarized inner lens mounted against rotation in front of the oculars of the eyeglasses, and a pair of polarized outer lenses mounted for rotation with respect to and in visual alignment with the oculars, the inner lens and outer lenses having their polarizing gratings in parallel for maximum light transmission when the outer lenses are at zero degrees rotation with respect to the inner lens, and the polarizing gratings being orthogonal for minimum light transmission when the outer lenses are at ninety degrees rotation with respect to the inner lens, said method comprising the steps of:

(a) providing an illuminated object for viewing;

(b) setting the outer lenses at zero degrees rotation with respect to the inner lens to permit maximum light transmission to the eyes;
(c) positioning the eyeglass in front of the patient's eyes;
(d) alternately occluding the eyes to identify the eye in which eye the illuminated object appears brighter, this eye being referred to as the unaffected eye and the other eye being referred to as the affected eye;
(e) rotating the adjacent outer lens for the unaffected eye away from zero degrees rotation with respect to the inner lens to decrease luminance until the illuminated object is sensed by the patient as being substantially equally bright in both eyes;
(f) quantifying the amount of rotation of the outer lens for the unaffected eye to thereby determine the amount of reduced brightness-sense of the affected eye as compared with the unaffected eye; and
(g) characterizing the amount of reduced brightness-sense of the affected eye in the range of approximately 80 to 100 percent of the unaffected eye as an indication for the absence of optic nerve disease.

3. A method of detecting eye disease in a patient by determining the difference in relative brightness sensed by the two eyes, using eyeglasses of the type having a polarized inner lens mounted against rotation in front of the oculars of the eyeglasses, and a pair of polarized outer lenses mounted for rotation with respect to and in visual alignment with the oculars, the inner lens and outer lenses having their polarizing gratings in parallel for maximum light transmission when the outer lenses are at zero degrees rotation with respect to the inner lens, and the polarizing gratings being orthogonal for minimum light transmission when the outer lenses are at ninety degrees rotation with respect to the inner lens, said method comprising the steps of:
(a) providing an illuminated object for viewing;
(b) setting the outer lenses at zero degrees rotation with respect to the inner lens to permit maximum light transmission to the eyes;
(c) positioning the eyeglasses in front of the patient's eyes;
(d) alternately occluding the eyes to identify the eye in which eye the illuminated object appears brighter, this eye being referred to as the unaffected eye and the other eye being referred to as the affected eye;
(e) rotating the adjacent outer lens for the unaffected eye away from zero degrees rotation with respect to the inner lens to decrease luminance until the illuminated object is sensed by the patient as being substantially equally bright in both eyes;
(f) quantifying the amount of rotation of the outer lens for the unaffected eye to thereby determine the amount of reduced brightness-sense of the affected eye as compared with the unaffected eye; and
(g) characterizing the amount of reduced brightness-sense of the affected eye in the range of approximately 2 to 40 percent of the unaffected eye, when accompanied by an increase in the amount of brightness-sense of the affected eye over approximately the next 4 to 8 months, as an indication for optic neuritis of recent onset.

4. A method of detecting eye disease in a patient by determining the difference in relative brightness sensed by the two eyes, using eyeglasses of the type having a polarized inner lens mounted against rotation in front of the oculars of the eyeglasses, and a pair of polarized outer lenses for rotation mounted with respect to and in visual alignment with the oculars, the inner lens and outer lenses having their polarizing gratings in parallel for maximum light transmission when the outer lenses are at zero degrees rotation with respect to the inner lens, and the polarizing gratings being orthogonal for minimum light transmission when the outer lenses are at ninety degrees rotation with respect to the inner lens, said method comprising the steps of:
(a) providing an illuminated object for viewing;
(b) setting the outer lenses at zero degrees rotation with respect to the inner lens to permit maximum light transmission to the eyes;
(c) positioning the eyeglasses in front of the patient's eyes;
(d) alternately occluding the eyes to identify the eye in which eye the illuminated object appears brighter, this eye being referred to as the unaffected eye and the other eye being referred to as the affected eye;
(e) rotating the adjacent outer lens for the unaffected eye away from zero degrees rotation with respect to the inner lens to decrease luminance until the illuminated object is sensed by the patient as being substantially equally bright in both eyes;
(f) quantifying the amount of rotation of the outer lens for the unaffected eye to thereby determine the amount of reduced brightness-sense of the affected eye as compared with the unaffected eye; and
(g) characterizing the amount of reduced brightness-sense of the affected eye in the range of approximately 25 to 75 percent of the unaffected eye, when accompanied by substantially normal vision for the patient and no substantial change in the amount of brightness-sense of the affected eye over approximately the next several months, as an indication for optic neuritis that is old or resolved.

5. A method of detecting eye disease in a patient by determining the difference in relative brightness sensed by the two eyes, using eyeglasses of the type having a polarized inner lens mounted against rotation in front of the oculars of the eyeglasses, and a pair of polarized outer lenses mounted for rotation with respect to and in visual alignment with the oculars, the inner lens and outer lenses having their polarizing gratings in parallel for maximum light transmission when the outer lenses are at zero degrees rotation with respect to the inner lens, and the polarizing gratings being orthogonal for minimum light transmission when the outer lenses are at ninety degrees rotation with respect to the inner lens, said method comprising the steps of:
(a) providing an illuminated object for viewing;
(b) setting the outer lenses at zero degrees rotation with respect to the inner lens to permit maximum light transmission to the eyes;
(c) positioning the eyeglasses in front of the patient's eyes;
(d) alternately occluding the eyes to identify the eye in which eye the illuminated object appears brighter, this eye being referred to as the unaffected eye and the other eye being referred to as the affected eye;
(e) rotating the adjacent outer lens for the unaffected eye away from zero degrees rotation with respect to the inner lens to decrease luminance until the illuminated object is sensed by the patient as being substantially equally bright in both eyes;

(f) quantifying the amount of rotation of the outer lens for the unaffected eye to thereby determine the amount of reduced brightness-sense of the affected eye as compared with the unaffected eye; and (g) characterizing the amount of reduced brightness-sense of the affected eye in the range of approximately 15 to 45 percent of the unaffected eye, when accompanied by an altitudinal visual field loss, as an indication for anterior ischemic optic neuropathy.

6. A method of detecting eye disease in a patient by determining the difference in relative brightness sensed by the two eyes, using eyeglasses of the type having a polarized inner lens mounted against rotation in front of the oculars of the eyeglasses, and a pair of polarized outer lenses mounted for rotation with respect to and in visual alignment with the oculars, the inner lens and outer lenses having their polarizing gratings in parallel for maximum light transmission when the outer lenses are at zero degrees rotation with respect to the inner lens, and the polarizing gratings being orthogonal for minimum light transmission when the outer lenses are at ninety degrees rotation with respect to the inner lens, said method comprising the steps of:

(a) providing an illuminated object for viewing;

(b) setting the outer lenses at zero degrees rotation with respect to the inner lens to permit maximum light transmission to the eyes;

(c) positioning the eyeglasses in front of the patient's eyes;

(d) alternately occluding the eyes to identify the eye in which eye the illuminated object appears brighter, this eye being referred to as the unaffected eye and the other eye being referred to as the affected eye;

(e) rotating the adjacent outer lens for the unaffected eye away from zero degrees rotation with respect to the inner lens to decrease luminance until the illuminated object is sensed by the patient as being substantially equally bright in both eyes;

(f) quantifying the amount of rotation of the outer lens for the unaffected eye to thereby determine the amount of reduced brightness-sense of the affected eye as compared with the unaffected eye; and (g) characterizing the amount of reduced brightness-sense of the affected eye in the range of approximately 1 to 35 percent of the unaffected eye, when accompanied by a reduction in the amount of brightness-sense of the affected eye over approximately the next several months, as an indication for compressive optic neuropathy (tumor).

7. A method of detecting eye disease in a patient by determining the difference in relative brightness sensed by the two eyes, using eyeglasses of the type having a polarized inner lens mounted against rotation in front of the oculars of the eyeglasses, and a pair of polarized outer lenses mounted for rotation with respect to and in visual alignment with the oculars, the inner lens and outer lenses having their polarizing gratings in parallel for maximum light transmission when the outer lenses are at zero degrees rotation with respect to the inner lens, and the polarizing gratings being orthogonal for minimum light transmission when the outer lenses are at ninety degrees rotation with respect to the inner lens, said method comprising the steps of:

(a) providing an illuminated object for viewing;

(b) setting the outer lenses at zero degrees rotation with respect to the inner lens to permit maximum light transmission to the eyes;

(c) positioning the eyeglasses in front of the patient's eyes;

(d) alternately occluding the eyes to identify the eye in which eye the illuminated object appears brighter, this eye being referred to as the unaffected eye and the other eye being referred to as the affected eye;

(e) rotating the adjacent outer lens for the unaffected eye away from zero degrees rotation with respect to the inner lens to decrease luminance until the illuminated object is sensed by the patient as being substantially equally bright in both eyes;

(f) quantifying the amount of rotation of the outer lens for the unaffected eye to thereby determine the amount of reduced brightness-sense of the affected eye as compared with the unaffected eye; and (g) characterizing the amount of reduced brightness-sense of the affected eye in the range of approximately 80 to 100 percent of the unaffected eye, when accompanied by poor visual acuity, as an indication for non-macular retinal disease.

8. A method of detecting eye disease in a patient by determining the difference in relative brightness sensed by the two eyes, using eyeglasses of the type having a polarized inner lens mounted against rotation in front of the oculars of the eyeglasses, and a pair of polarized outer lenses mounted for rotation with respect to and in visual alignment with the oculars, the inner lens and outer lenses having their polarizing gratings in parallel for maximum light transmission when the outer lenses are at zero degrees rotation with respect to the inner lens, and the polarizing gratings being orthogonal for minimum light transmission when the outer lenses are at ninety degrees rotation with respect to the inner lens, said method comprising the steps of:

(a) providing an illuminated object for viewing;

(b) setting the outer lenses at zero degrees rotation with respect to the inner lens to permit maximum light transmission to the eyes;

(c) positioning the eyeglasses in front of the patient's eyes;

(d) alternately occluding the eyes to identify the eye in which eye the illuminated object appears brighter, this eye being referred to as the unaffected eye and the other eye being referred to as the affected eye;

(e) rotating the adjacent outer lens for the unaffected eye away from zero degrees rotation with respect to the inner lens to decrease luminance until the illuminated object is sensed by the patient as being substantially equally bright in both eyes;

(f) quantifying the amount of rotation of the outer lens for the unaffected eye to thereby determine the amount of reduced brightness-sense of the affected eye as compared with the unaffected eye; and (g) characterizing the amount of reduced brightness-sense of the affected eye in the range of approximately 35 to 85 percent of the unaffected eye, when accompanied by poor visual acuity, as an indication for macular retinal disease.

9. A system for detecting eye disease eye disease in a patient by determining the difference in relative brightness sensed by the two eyes, comprising:

(a) an illuminated object for viewing;

(b) a pair of eyeglasses for mounting in front of the patient's eyes, said pair of eyeglasses including,
a substantially transparent polarized mounted against rotation with respect to said frame, said inner lens being mounted in visual alignment with the patient's eyes;
a pair of substantially transparent polarized outer lenses mounted for rotating with respect to said frame, with one outer lens in visual alignment with and rotatable with respect to one eye and the other outer lens in visual alignment with and rotatable with respect to the other eye;
rotation of said pair of outer lenses with respect to said inner lens over a ninety degree angle varying the amount of brightness sensed by the eyes when viewing said illuminated object, selective independent rotation of one of said pair of outer lenses with respect to the other causing the amount of brightness sensed by one eye to be substantially the same as the amount of brightness sensed by the other eye; and
means for quantifying the amount that the outer lens of one eye has rotated relative to the inner lens and the amount that the outer lens of the other eye has rotated with respect to the inner lens when the amount of brightness sensed by each eye is substantially equal, to thereby determine the relative sense of brightness of the two eyes; and (c) means for characterizing the amount of reduced brightness-sense of one eye as compared to the other eye as an indication of eye disease in the eye for which said illuminated object appeared less bright according to the following table:

| TYPE OF EYE DISEASE | AMOUNT OF RE-DUCED BRIGHT-NESS-SENSE OF AFFECTED EYE (%) | OTHER CONSIDERATIONS |
| --- | --- | --- |
| No disease | 80–100 | No significant inter-eye brightness-sense disparity |
| Optic neuritis (recent onset) | 2–40 | Brightness-sense increase over next 4–8 months |
| Optic neuritis (old/resolved) | 25–75 | 20/20 vision; no change in brightness-sense |
| Anterior ischemic optic neuropathy | 15–45 | Accompanied by altitudnal visual field loss |
| Compressive optic neuropathy | 1–35 | Brightness-sense reduction over next several months |
| Retinal diseases (non-macular) | 80–100 | Accompanied by poor visual acuity |
| Retinal diseases (macular) | 35–85 | Accompanied by poor visual acuity |
| Cataracts | 80–100 | No significant inter-eye brightness-sense disparity |

* * * * *